United States Patent
Nakano

(10) Patent No.: US 9,708,569 B2
(45) Date of Patent: Jul. 18, 2017

(54) FRAGRANCE COMPOSITION AND METHOD FOR PRODUCING SAME

(71) Applicant: ZEON CORPORATION, Tokyo (JP)

(72) Inventor: Keita Nakano, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 0 days.

(21) Appl. No.: 14/779,421

(22) PCT Filed: Mar. 17, 2014

(86) PCT No.: PCT/JP2014/057183
§ 371 (c)(1),
(2) Date: Sep. 23, 2015

(87) PCT Pub. No.: WO2014/156783
PCT Pub. Date: Oct. 2, 2014

(65) Prior Publication Data
US 2016/0046888 A1    Feb. 18, 2016

(30) Foreign Application Priority Data
Mar. 29, 2013   (JP) .................................. 2013-075382

(51) Int. Cl.
*C11B 9/00* (2006.01)
*C07C 67/54* (2006.01)

(52) U.S. Cl.
CPC .............. *C11B 9/003* (2013.01); *C07C 67/54* (2013.01); *C07C 2101/08* (2013.01)

(58) Field of Classification Search
CPC .................................................... C11B 9/003
See application file for complete search history.

(56) References Cited

U.S. PATENT DOCUMENTS

| 4,260,830 A | 4/1981 | Wilson et al. |
| 5,235,110 A * | 8/1993 | Yamada ................. C07C 49/395 512/8 |

(Continued)

FOREIGN PATENT DOCUMENTS

| JP | 56-147740 A | 11/1981 |
| JP | 61-37756 A | 2/1986 |

(Continued)

OTHER PUBLICATIONS

Written Opinion of the International Searching Authority dated May 27, 2014, for International Application No. PCT/JP2014/057183.
International Search Report, issued in PCT/JP2014/057183, dated May 27, 2014.

*Primary Examiner* — Lanee Reuther
(74) *Attorney, Agent, or Firm* — Birch, Stewart, Kolasch & Birch, LLP

(57) ABSTRACT

The present invention is a fragrance composition comprising methyl dihydrojasmonate and a compound (I), the fragrance composition containing 94.5 to 99% by mass of the methyl dihydrojasmonate and 1 to 5% by mass of the compound (I), the methyl dihydrojasmonate. In addition, the present invention is a method for producing the fragrance composition, the method comprising subjecting a composition that contains methyl dihydrojasmonate and the compound (I) sequentially to a concentration distillation step and a thin film distillation step, the composition containing 90 to 99.5% by mass of the methyl dihydrojasmonate and 0.1 to 1.5% by mass of the compound (I), the methyl dihydrojasmonate having a cis isomer content of less than 20 mol %.

(Continued)

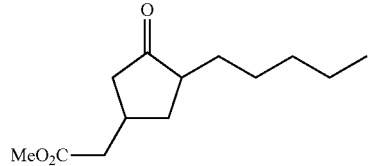

Compound (I)

5 Claims, 1 Drawing Sheet

(56) References Cited

U.S. PATENT DOCUMENTS 5,372,994 A 12/1994 Yamada et al.
2004/0171850 A1 9/2004 Mine et al.

FOREIGN PATENT DOCUMENTS

| JP | 6137756 A * | 2/1986 | ............ C07C 67/32 |
| JP | 3-188194 A | 8/1991 | |
| JP | 5-37140 B2 | 6/1993 | |
| JP | 2002-60781 A | 2/2002 | |
| JP | 2002-69477 A | 3/2002 | |
| JP | 2004-217619 A | 8/2004 | |

* cited by examiner

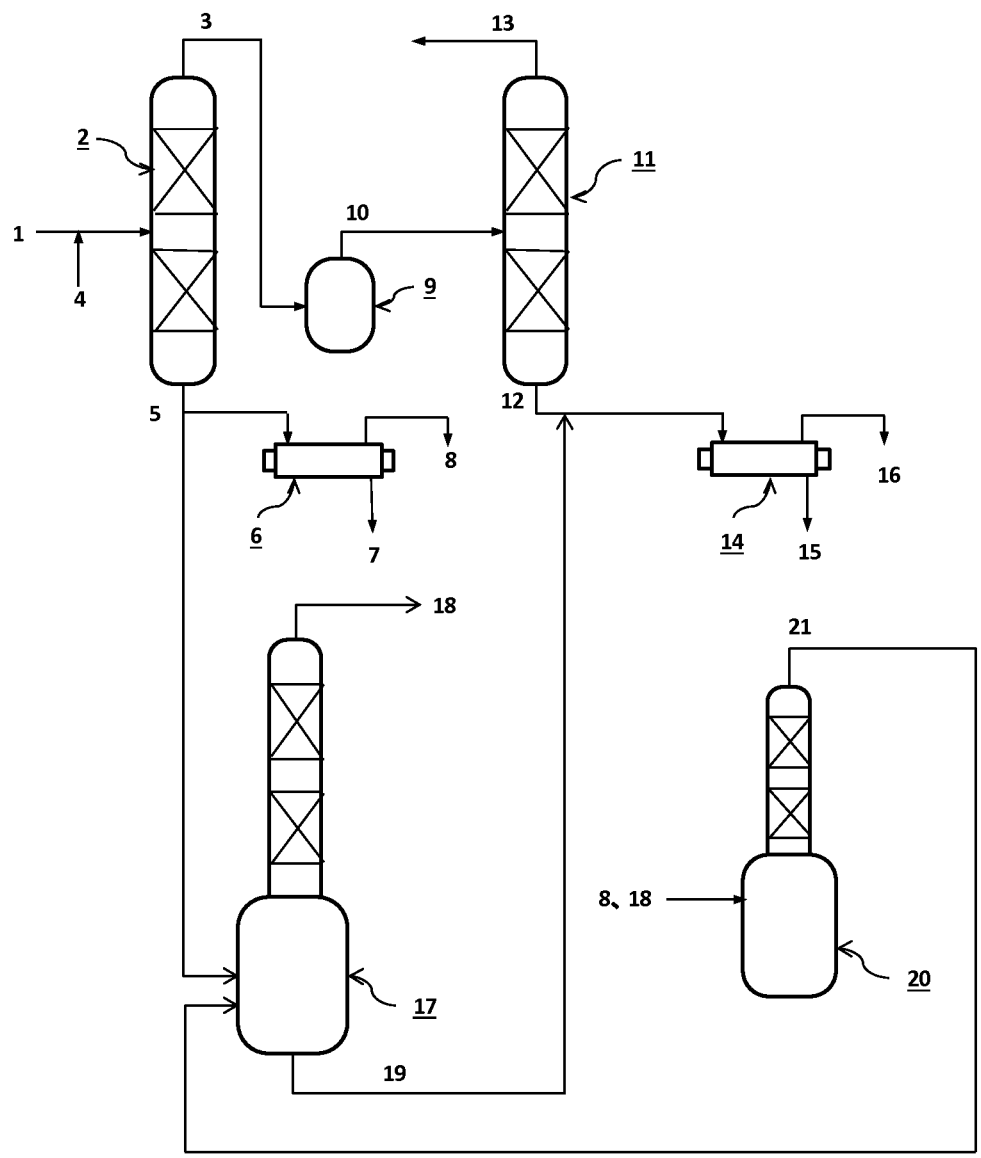

FRAGRANCE COMPOSITION AND METHOD FOR PRODUCING SAME

TECHNICAL FIELD

The present invention relates to a fragrance composition that includes methyl dihydrojasmonate having a high specific stereoisomer content as a main component, and a method for producing the same.

BACKGROUND ART

An alkyl dihydrojasmonate has been known as a useful fragrance compound due to excellent smell intensity. A method for producing an alkyl dihydrojasmonate and the like are disclosed in various documents (see Patent Documents 1 to 3, for example).

Patent Document 4 discloses that a mixture of alkyl dihydrojasmonates obtained using a mixture (raw material) that includes a 2-substituted 2-cyclopentenone and a 2-substituted 4-cyclopentenone in a ratio of 70 to 95:5 to 30 exhibits excellent fragrance properties (e.g., spreading and lingering properties) as compared with the case where the alkyl dihydrojasmonates are used alone.

Patent Document 5 discloses that an alkyl jasmonate in the form of a cis isomer (epi isomer) is useful as a fragrance as compared with an alkyl jasmonate in the form of a trans isomer, and discloses a method that produces an alkyl jasmonate having a high cis isomer content from an alkyl jasmonate having a low cis isomer content.

RELATED-ART DOCUMENT

Patent Document

Patent Document 1: JP-A-56-147740
Patent Document 2: JP-A-2004-217619 (US20040171850A1)
Patent Document 3: JP-A-2002-60781
Patent Document 4: JP-B-5-37140
Patent Document 5: JP-A-2002-69477

SUMMARY OF THE INVENTION

Technical Problem

An object of the invention is to provide a fragrance composition that includes methyl dihydrojasmonate having a high specific stereoisomer content as the main component, and produces a high-quality lingering jasmine-like smell that is rich and deep, and a method for producing the same.

Solution to Problem

The inventor of the invention conducted extensive studies in order to achieve the above object. As a result, the inventor found that a fragrance composition that contains methyl dihydrojasmonate having a cis isomer content of 20% or more as the main component, and contains the following compound (I) in a ratio of 1 to 5 mass % based on the total amount of the fragrance composition, produces a high-quality lingering jasmine-like smell that is rich and deep.

The inventor also found that the fragrance composition can be easily and efficiently obtained by subjecting a composition that contains methyl dihydrojasmonate having a low cis isomer content and the compound (I) in a specific ratio sequentially to an isomerization step, a concentration distillation step, and a thin film distillation step. These findings have led to the completion of the invention.

Several aspects of the invention provide the following fragrance composition (see (a) and (b)) and method for producing a fragrance composition (see (c) to (e)).

(a) A fragrance composition comprising methyl dihydrojasmonate and a compound (I), the fragrance composition containing 94.5 to 99% by mass of the methyl dihydrojasmonate and 1 to 5% by mass of the compound (I), the methyl dihydrojasmonate having a cis isomer content of 20 mol % or more,

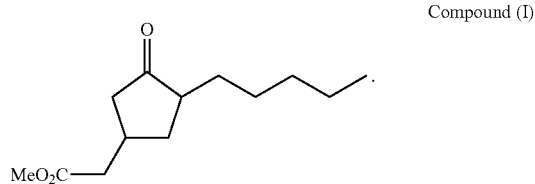 [SMILES: CCCCCC1CC(CC(=O)OC)CC1=O]

Compound (I)

(b) The fragrance composition according to (a), the fragrance composition being obtained by mixing a fragrance composition that contains 99% or more by mass of methyl dihydrojasmonate having a cis isomer content of 20 mol % or more and less than 1% by mass of the compound (I), with a fragrance composition that contains 70 to 94.5% by mass of methyl dihydrojasmonate having a cis isomer content of 20 mol % or more and 5 to 30% by mass of the compound (I).

(c) A method for producing the fragrance composition according to (a), the method comprising subjecting a composition (A) that comprises methyl dihydrojasmonate having a cis isomer content of 20 mol % or more and the compound (I) sequentially to a concentration distillation step and a thin film distillation step, the composition (A) containing 90 to 99.5% by mass of the methyl dihydrojasmonate and 0.1 to 1.5% by mass of the compound (I).

(d) The method according to (c), wherein the composition (A) is a high-boiling fraction (5) that is obtained from a bottom of a purification distillation column when a reaction mixture (1) is fed to the purification distillation column to effect purification distillation, the reaction mixture (1) containing methyl dihydrojasmonate having a cis isomer content of less than 20 mol % as a main component, the methyl dihydrojasmonate being obtained by reacting dimethyl malonate with a raw material composition that comprises 2-pentyl-2-cyclopentenone and 2-pentyl-4-cyclopentenone in a mass ratio (2-pentyl-2-cyclopentenone:2-pentyl-4-cyclopentenone) of 95.5:4.5 to 99.5:0.5, followed by decarboxylation.

(e) The method according to (d), wherein the composition (A) is a low-boiling fraction (21) that is obtained from a top of a purification distillation column when a mixture is fed to an isomerization reactor to effect isomerization, and fed to the purification distillation column to effect purification distillation, the mixture comprising a low-boiling fraction (18) that is obtained from a top of a concentration distillation column when the high-boiling fraction (5) that is obtained from the bottom of the purification distillation column when the reaction mixture (1) is fed to the purification distillation column to effect purification distillation is fed to the concentration distillation column to effect concentration distillation and a fraction that is obtained from a top of a thin film evaporator when the high-boiling fraction (5) obtained from the bottom of the purification distillation column is fed to the thin film evaporator, the reaction mixture (1) comprising methyl dihydrojasmonate having a cis isomer content of less than 20 mol % as a main component, the methyl dihydrojasmonate being obtained by reacting dimethyl malonate with the raw material composition that comprises 2-pentyl-2-cyclopentenone and 2-pentyl-4-cyclopentenone in the mass ratio (2-pentyl-2-cyclopentenone:2-pentyl-4-cyclopentenone) of 95.5:4.5 to 99.5:0.5, followed by the decarboxylation.

Advantageous Effects of the Invention

The fragrance composition according to one aspect of the invention produces a high-quality lingering jasmine-like smell that is rich and deep.

The production method according to one aspect of the invention can easily and efficiently produce the fragrance composition according to one aspect of the invention.

Since the production method according to one aspect of the invention utilizes the MDJ fraction having a low cis isomer content that is obtained (in a large quantity) by the concentration distillation step, it is possible to significantly improve the total production efficiency (productivity).

BRIEF DESCRIPTION OF DRAWINGS

FIG. 1 is a schematic view illustrating a production process used to obtain each fraction used in connection with the embodiments of the invention.

DESCRIPTION OF EMBODIMENTS

A fragrance composition and a method for producing a fragrance composition according to exemplary embodiments of the invention are described in detail below.
1) Fragrance Composition A fragrance composition according to one embodiment of the invention includes methyl dihydrojasmonate (hereinafter may be abbreviated as "MDJ") and the compound (I), the fragrance composition containing 94.5 to 99% by mass of the MDJ and 1 to 5% by mass of the compound (I) and the MDJ having a cis isomer content of 20 mol % or more.

The MDJ included in the fragrance composition according to one embodiment of the invention may be present in the form of the four stereoisomers represented by the following formulas (1-a) to (1-d). The compound represented by the formula (1-a) and the compound represented by the formula (1-b) are collectively referred to as "cis isomer", and the compound represented by the formula (1-c) and the compound represented by the formula (1-d) are collectively referred to as "trans isomer".

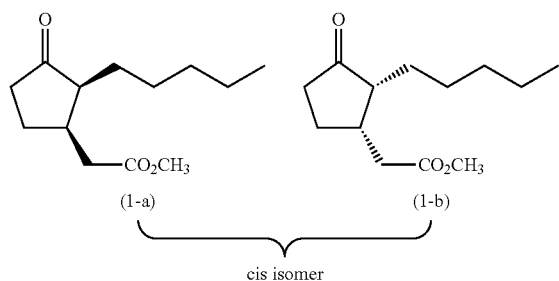

cis isomer

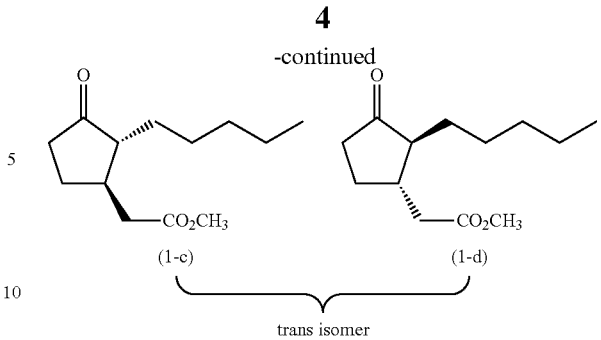

trans isomer

The fragrance composition according to one embodiment of the invention contains 94.5 to 99% by mass of the MDJ and preferably 96 to 98.8% by mass.

The cis isomer content ((amount of cis isomer)/(amount (mol) of cis isomer+amount (mol) of trans isomer)×100 (mol %)) in the MDJ contained in the fragrance composition according to one embodiment of the invention is not particularly limited as long as the cis isomer content is 20 mol % or more. The cis isomer content in the MDJ included in the fragrance composition according to one embodiment of the invention is preferably 20 to 50 mol %, and more preferably 30 to 45 mol %.

The fragrance composition according to one embodiment of the invention contains 1 to 5% by mass of the compound (I) and preferably 2 to 4% by mass. If the ratio of the compound (I) is less than 1 mass %, the resulting fragrance composition may not produce a rich smell. If the ratio of the compound (I) exceeds 5 mass %, the resulting fragrance composition may produce a heavy and oily smell.

When the cis isomer content in the MDJ and the ratio of the compound (I) are within the above ranges, the resulting fragrance composition produces a high-quality lingering jasmine-like smell that is rich and deep.

Note that the compound (I) may be present in the form of four stereoisomers in the same manner as MDJ, and the total content of these stereoisomers is taken as the content of the compound (I).

The fragrance composition according to one embodiment of the invention produces a high-quality lingering jasmine-like smell that is rich and deep. The fragrance composition according to one embodiment of the invention is useful as an aroma component that produces a strong jasmine-like smell, and is used as a perfume, a cosmetic preparation, and a food flavor.
2) Method for Producing Fragrance Composition A method for producing a fragrance composition according to one embodiment of the invention includes subjecting a composition (A) that includes MDJ and the compound (I) sequentially to a concentration distillation step and a thin film distillation step, the composition (A) containing 90 to 99.5% by mass of the MDJ and 0.1 to 1.5% by mass of the compound (I), the MDJ having a cis isomer content of less than 20 mol % (preferably 1.5 to 12 mol %).

Each fraction obtained using the method disclosed in Patent Document 5 may be used directly as the composition (A), or the composition (A) may be prepared by appropriately mixing each fraction obtained using the method disclosed in Patent Document 5, for example.

Specific examples of the composition (A) include the following fractions (mixtures) (i) to (vii).

(i) A high-boiling fraction (5) that is obtained from the bottom of a purification distillation column by feeding a reaction mixture (1) to the purification distillation column to effect purification distillation, the reaction mixture (1)

containing methyl dihydrojasmonate having a cis isomer content of less than 20 mol % as a main component, the methyl dihydrojasmonate being obtained by reacting dimethyl malonate with a raw material composition (B) that includes 2-pentyl-2-cyclopentenone and 2-pentyl-4-cyclopentenone in a mass ratio (2-pentyl-2-cyclopentenone:2-pentyl-4-cyclopentenone) of 95.5:4.5 to 99.5:0.5 (Michael addition), followed by decarboxylation.

(ii) A mixture that includes a low-boiling fraction (3) that is obtained from the top of a purification distillation column by feeding the reaction mixture (1) to the purification distillation column to effect purification distillation, and a high-boiling fraction (5) that is obtained from the bottom of a purification distillation column by feeding the reaction mixture (1) to the purification distillation column to effect purification distillation.

(iii) A mixture that includes a low-boiling fraction (13) that is obtained from the top of a concentration distillation column by isomerizing a low-boiling fraction (3) that is obtained from the top of a purification distillation column by feeding the reaction mixture (1) to the purification distillation column to effect purification distillation, and feeding the reaction mixture obtained by isomerization to the concentration distillation column to effect concentration distillation, and a high-boiling fraction (5) that is obtained from the bottom of a purification distillation column by feeding the reaction mixture (1) to the purification distillation column to effect purification distillation.

(iv) A low-boiling fraction (8) that is obtained from the top of a thin film distillation column by feeding a high-boiling fraction (5) to the thin film distillation column to effect thin film distillation. The high-boiling fraction (5) is obtained from the bottom of the purification distillation column by feeding the reaction mixture (1) to the purification distillation column to effect purification distillation.

(v) A mixture that includes a low-boiling fraction (13) that is obtained from the top of a concentration distillation column by isomerizing a low-boiling fraction (3) that is obtained from the top of a purification distillation column by feeding the reaction mixture (1) to the purification distillation column to effect purification distillation, and feeding the reaction mixture obtained by isomerization to the concentration distillation column to effect concentration distillation, and a low-boiling fraction (8) that is obtained from the top of a thin film distillation column by feeding a high-boiling fraction (5) that is obtained from the bottom of a purification distillation column by feeding the reaction mixture (1) to the purification distillation column to effect purification distillation to the thin film distillation column to effect thin film distillation.

(vi) A mixture that includes a low-boiling fraction (8) and a low-boiling fraction (18). The low-boiling fraction (8) is obtained from the top of a thin film distillation column by feeding a high-boiling fraction (5) to the thin film distillation column to effect thin film distillation. The high-boiling fraction (5) is obtained from the bottom of a purification distillation column by feeding the reaction mixture (1) to the purification distillation column to effect purification distillation. The low-boiling fraction (18) is obtained from the top of a concentration distillation column by feeding the high-boiling fraction (5) to the concentration distillation column to effect concentration distillation.

(vii) A low-boiling fraction (21) that is obtained from the top of a purification distillation column by feeding a mixture that includes a low-boiling fraction (8) and a low-boiling fraction (18) to an isomerization reactor to effect isomerization, and feeding the reaction mixture to the purification distillation column to effect purification distillation, the low-boiling fraction (8) being obtained from the top of a thin film distillation column by feeding a high-boiling fraction (5) that is obtained from the bottom of a purification distillation column by feeding the reaction mixture (1) to the purification distillation column to effect purification distillation to the thin film distillation column to effect thin film distillation, and the low-boiling fraction (18) being obtained from the top of a concentration distillation column by feeding a high-boiling fraction (5) that is obtained from the bottom of a purification distillation column by feeding the reaction mixture (1) to the purification distillation column to effect purification distillation to the concentration distillation column to effect concentration distillation.

The raw material composition (B) may be prepared using a known method such as a method that reacts cyclopentanone and valeraldehyde in the presence of a base catalyst (e.g., sodium hydroxide) (aldol reaction and dehydration), and heats the resulting reaction mixture in an appropriate solvent (e.g., butanol) in the presence of hydrochloric acid (catalyst) to effect dehydration and isomerization (dehydration and isomerization) (see Patent Documents 1 and 2, for example).

The reaction mixture (1) is a mixture that includes MDJ as a main component, the MDJ being obtained by reacting dimethyl malonate with the raw material composition (B) using a known method (see Patent Documents 1 and 2, for example), followed by decarboxylation. The reaction mixture (1) normally includes the MDJ in a ratio of 80 to 99 mass % based on the total amount of the reaction mixture (1), and the MDJ normally has a cis isomer content of 12 mol % or less.

FIG. 1 is a schematic view illustrating the process used to obtain each fraction used in connection with the embodiments of the invention.

In FIG. 1, reference numeral 2 indicates a purification distillation column, reference numeral 9 indicates an isomerization reactor, reference numeral 11 indicates a concentration distillation column, reference numerals 6 and 14 indicate a thin film evaporator, reference numeral 17 indicates a batch-type concentration distillation column, and reference numeral 20 indicates a batch-type isomerization reactor-purification distillation column.

The methods for obtaining the fractions (mixtures) (i) to (vii) are described in detail below with reference to FIG. 1.

Purification Distillation Step

The reaction mixture (1) obtained as described above is fed to the purification distillation column 2 to effect purification distillation.

It is preferable to use a packed column that is charged with a Sulzer packing (i.e., a packing in which mesh strips formed by a stainless steel wire are integrally arranged in parallel) as the purification distillation column 2.

The purification distillation step is normally performed under reduced pressure since a high-boiling compound is subjected to distillation. The degree of decompression is normally set to −90 to −101.3 kPaG, and preferably −95 to −101.1 kPaG, the column top temperature is normally set to 100 to 120° C., and preferably 105 to 110° C., and the column bottom temperature is normally set to 160 to 190° C., and preferably 170 to 180° C.

The reaction mixture (1) is fed to the middle of the purification distillation column 2, and the high-boiling fraction (5) is extracted from the bottom of the purification distillation column 2 in a ratio of about 80 to 90 mass % with respect to the amount of the reaction mixture (1) fed to the purification distillation column 2.

The low-boiling fraction (3) is extracted from the top of the purification distillation column 2 in a ratio of about 10 to 20 mass % with respect to the amount of the reaction mixture (1) fed to the purification distillation column 2.

The low-boiling fraction (3) normally contains 93 to 96% by mass of the MDJ based on the total amount of the low-boiling fraction (3), the MDJ normally has a cis isomer content of 1.5 to 4.5 mol %, and the low-boiling fraction (3) normally contains 0.05 to 0.30% by mass of the compound (I) based on the total amount of the low-boiling fraction (3).

The low-boiling fraction (3) may be subjected to the isomerization step and the concentration distillation step described later, and used as part of the fraction (iii) or (v).

The high-boiling fraction (5) normally contains 97 to 99% by mass of the MDJ based on the total amount of the high-boiling fraction (5), the MDJ normally has a cis isomer content of 10 to 12 mol %, and the high-boiling fraction (5) normally contains 0.5 to 1.2% by mass of the compound (I) based on the total amount of the high-boiling fraction (5).

The high-boiling fraction (5) is used as the composition (A) (see (i)). Alternatively, the high-boiling fraction (5) is mixed with the low-boiling fraction (3), and the resulting mixture is used as the composition (A) (see (ii)). Note that the mixing ratio of the high-boiling fraction (5) and the low-boiling fraction (3) must be appropriately adjusted when using a mixture that includes the high-boiling fraction (5) and the low-boiling fraction (3) as the composition (A) (see (ii)).

The high-boiling fraction (5) may be mixed with a fraction obtained by subjecting the low-boiling fraction (3) to the isomerization step and the concentration distillation step described later, and the resulting mixture may be used as the composition (A) (see (iii)).

Purification distillation is also effected using the batch-type isomerization reactor-purification distillation column 20.

The column bottom temperature is normally set to 160 to 190° C., and preferably 170 to 180° C.

The pressure inside the purification distillation column is not particularly limited, but is normally set to −90 to −101.3 kPaG, and preferably −95 to −101.1 kPaG.

A fraction (21) that contains 94 to 99.9% by mass of the MDJ (cis isomer content in MDJ: 10 mol % or more (normally 10 to 12 mol %)) is extracted from the batch-type isomerization reactor-purification distillation column 20, and fed to the concentration distillation column 17.

Isomerization Step

The cis isomer content in the MDJ can be increased by subjecting the low-boiling fraction (3) (or the low-boiling fractions (8) and (18)) to the isomerization step.

Isomerization is effected by heating the low-boiling fraction (3) in the isomerization reactor 9 in the presence of a base or an acid, or heating the product MDJ (8) and the low-boiling fraction (18) (described later) in the batch-type isomerization reactor-purification distillation column 20 in the presence of a base or an acid.

Examples of the base include an alkali metal carbonate such as sodium carbonate and potassium carbonate; an alkali metal hydrogen carbonate such as sodium hydrogen carbonate and potassium hydrogen carbonate; an alkaline-earth metal carbonate such as calcium carbonate and magnesium carbonate; an alkaline-earth metal hydrogen carbonate such as calcium hydrogen carbonate; an alkali metal hydroxide such as sodium hydroxide and potassium hydroxide; an alkaline-earth metal hydroxide such as magnesium hydroxide and calcium hydroxide; and the like.

Examples of the acid include an ion-exchange resin (e.g., Diaion, Dowex, and Amberlite); an inorganic acid such as hydrochloric acid, sulfuric acid, and phosphoric acid; an organic acid such as acetic acid, tosylic acid, and oxalic acid; and the like.

The base or acid catalyst is normally used in an amount of 10 to 1,000 ppm, and preferably 50 to 200 ppm, based on the MDJ, taking account of the type of the catalyst.

Isomerization may be effected in the presence of a solvent. Note that it is preferable to effect isomerization in the absence of a solvent.

Isomerization in the isomerization reactor 9 is normally effected while setting the heating temperature to 160 to 190° C. (preferably 175 to 177° C.), and setting the heating time to about 5 to 11 hours. The pressure inside the reaction system is not particularly limited, but is normally set to −90 to −101.3 kPaG, and preferably −95 to −101.1 kPaG.

A gaseous product (10) that contains 94 to 98% by mass of the MDJ (cis isomer content in MDJ: 10 mol % or more (normally 10 to 12 mol %)) is continuously extracted from the isomerization reactor 9 in a ratio of about 10 to 20 mass % with respect to the amount of the reaction mixture (1) fed to the purification distillation column 2, and fed to the concentration distillation column 11.

Isomerization in the batch-type isomerization reactor-purification distillation column 20 is normally effected while setting the heating temperature to 160 to 190° C. (preferably 170 to 180° C.), and setting the heating time to about 1 to 10 hours. The pressure inside the reaction system is not particularly limited, but is normally set to −50 to +100 kPaG, and preferably 0 to 50 kPaG.

Concentration Distillation Step

The concentration distillation step is normally performed in order to increase the cis isomer content in the MDJ. Specifically, the gaseous product (10) extracted from the isomerization reactor 9 is subjected to concentration distillation using the concentration distillation column 11. The high-boiling fraction (5) extracted from the purification distillation column 2 is subjected to concentration distillation using the batch-type concentration distillation column 17.

It is preferable to use a distillation column charged with a Sulzer packing as the concentration distillation column (in the same manner as the purification distillation column 2).

The feed rate of the gaseous product 10 that is fed to the concentration distillation column is not particularly limited, but is normally 35 to 50 parts by mass per hour. The average dwell time is normally 6 to 10 hours.

The pressure inside the concentration distillation column 11 and the batch-type concentration distillation column 17 is normally set to −90 to −101.3 kPaG, and preferably −95 to −101.1 kPaG, the column bottom temperature is normally set to 160 to 185° C., and preferably 165 to 180° C., and the column top temperature is normally set to 100 to 150° C., and preferably 105 to 140° C.

The low-boiling fraction (13) is continuously extracted from the top of the concentration distillation column 11 in a ratio of about 80 to 90 mass % with respect to the amount of the gaseous product (10) fed to the concentration distillation column 11. The low-boiling fraction (13) normally contains 91 to 95% by mass of the MDJ based on the total amount of the low-boiling fraction (13), the MDJ normally has a cis isomer content of 2 to 4 mol %, and the low-boiling fraction (13) normally contains less than 0.1% by mass of the compound (I) based on the total amount of the low-boiling fraction (13).

The low-boiling fraction (13) is mixed with the high-boiling fraction (5), and the resulting mixture is used as the composition (A) (see (iii)).

The low-boiling fraction (18) extracted from the top of the batch-type concentration distillation column 17 is fed to the batch-type isomerization reactor-purification distillation column 20. The low-boiling fraction (18) normally contains 95 to 100% by mass of the MDJ based on the total amount of the low-boiling fraction (18), the MDJ normally has a cis isomer content of 2 to 4 mol %, and the low-boiling fraction (18) normally contains less than 0.1% by mass of the compound (I) based on the total amount of the low-boiling fraction (13).

A high-boiling fraction (12) (cis isomer content in MDJ: 30 to 43 mol %) is extracted from the bottom of the concentration distillation column 11 at a rate of about 4 to 8 parts by mass per hour. A high-boiling fraction (19) (cis isomer content in MDJ: 30 to 43 mol %) is extracted from the bottom of the batch-type concentration distillation column 17. The high-boiling fraction (12) and the high-boiling fraction (19) are subjected to the subsequent thin film distillation step.

The low-boiling fraction (13) is mixed with the high-boiling fraction (5), and the resulting mixture is used as the composition (A) (see (iii)). Alternatively, the low-boiling fraction (13) is mixed with the fraction (8) (product MDJ) obtained by the thin film distillation step (described later), and the resulting mixture is used as the composition (A) (see (v)). The low-boiling fraction (18) is mixed with the fraction (8) (product MDJ) obtained by the thin film distillation step (described later), and the resulting mixture is used as the composition (A) (see (vi)).

The mixing ratio is adjusted so that the composition (A) normally contains 94 to 98% by mass of the MDJ based on the total amount of the composition (A), the MDJ normally has a cis isomer content of 2.5 to 12 mol %, and the composition (A) normally contains 0.2 to 1.2% by mass of the compound (I) based on the total amount of the composition (A).

It is possible to significantly improve the production efficiency by effectively utilizing the MDJ fraction having a low cis isomer content that is obtained (in a large quantity) by the concentration distillation step.

Thin Film Distillation Step

The high-boiling fraction (5) is fed to the thin film evaporator 6, and subjected to thin film distillation.

The thin film distillation process has advantages in that the distillation target liquid in the form of a thin film can be distilled under vacuum at a lower temperature (i.e., while preventing a thermal effect), and a trace amount of high-boiling impurities, a component that produces an abnormal odor, and the like that remain in the still after completion of concentration distillation can be easily removed.

The pressure inside the thin film evaporator 6 is normally set to −90 to −101.3 kPaG, and preferably −95 to −101.3 kPaG, and the distillation temperature is normally set to 135 to 145° C.

The fraction (8) (product MDJ) is extracted from the top of the thin film evaporator 6 (thin film distillation column) in a ratio of about 77 to 87 mass % with respect to the amount of the reaction mixture (1) fed to the purification distillation column 2.

The fraction (8) (product MDJ) is used as the composition (A) (see (iv)). A mixture that includes the fraction (8) and the low-boiling fraction (13) may also be used as the composition (A) (see (v)), and a mixture that includes the fraction (8) and the low-boiling fraction (18) may also be used as the composition (A) (see (vi)).

The fraction (8) normally contains 97.5 to 99.5% by mass of the MDJ based on the total amount of the fraction (8), the MDJ normally has a cis isomer content of 10 to 12 mol %, and the fraction (8) normally contains 0.5 to 1.5% by mass of the compound (1) based on the total amount of the fraction (8).

Note that a high-boiling fraction (7) that includes high-boiling impurities is continuously extracted from the bottom of the thin film evaporator 6 in a ratio of about 3 to 13 mass % with respect to the amount of the reaction mixture (1) fed to the purification distillation column 2. The high-boiling fraction (7) is disposed of, and is optionally returned to a raw material system 4 that is fed to the purification distillation column 2. This makes it possible to improve the production efficiency and reduce the amount of waste.

The fragrance composition according to one embodiment of the invention can be obtained by the thin film distillation effected using the thin film evaporator 14. The target fragrance composition (16) according to one embodiment of the invention is extracted from the top of the thin film evaporator 14 at a rate of 5 to 6.5 parts by mass per hour within 10 hours from the start of thin film distillation.

The temperature of vapor obtained by thin film distillation is normally 135 to 145° C., and preferably 138 to 142° C., and the pressure inside the thin film evaporator 14 is normally set to −95 to −101.3 kPaG.

Note that a high-boiling fraction (15) that includes high-boiling impurities is continuously extracted from the bottom of the thin film evaporator 14 at a rate of 0.1 to 0.5 parts by mass per hour. The high-boiling fraction (15) is disposed of, and is optionally returned to the raw material system 4 that is fed to the purification distillation column 2. This makes it possible to improve the production efficiency and reduce the amount of waste.

Composition (A)

The target fragrance composition according to one embodiment of the invention can be obtained by subjecting the composition (A) (see (i) to (vii), for example) sequentially to the concentration distillation step and the thin film distillation step, or the isomerization step, the purification distillation step, the concentration distillation step, and the thin film distillation step (see FIG. 1). The target fragrance composition according to one embodiment of the invention can also be obtained by effecting the isomerization step and the concentration distillation step in a batch-wise manner.

The fragrance composition according to one embodiment of the invention includes methyl dihydrojasmonate (MDJ) and the compound (I), the fragrance composition containing 94.5 to 99% by mass of the MDJ and 1 to 5% by mass of the compound (I) and the MDJ having a cis isomer content of 20 mol % or more. The fragrance composition according to one embodiment of the invention can be produced using the above method. The fragrance composition according to one embodiment of the invention can also be obtained by mixing a fragrance composition that contains 99% or more by mass of methyl dihydrojasmonate having a cis isomer content of 20 mol % or more and less than 1% by mass of the compound (I), with a fragrance composition that contains 70 to 94.5% by mass of methyl dihydrojasmonate having a cis isomer content of 20 mol % or more and 5 to 30% by mass of the compound (I).

EXAMPLES

The invention is further described below by way of examples. Note that the invention is not limited to the following examples.

Production Example 1

Cyclopentanone and valeraldehyde were reacted in the presence of sodium hydroxide (catalyst) using a known method (see Patent Documents 1 and 2, for example) to obtain an aldol product, which was subjected to dehydration and isomerization in butanol (solvent) in the presence of hydrochloric acid (catalyst) to produce 2-pentyl-2-cyclopentenone (PPEN). The reaction mixture was purified by distillation to obtain a raw material composition (B1) (PPEN content: 98.6 mass %, PPEN:2-pentyl-4-cyclopentene=98.7:1.3).

Example 1

Dimethyl malonate was reacted with the raw material composition (B1) obtained in Production Example 1 (Michael addition) using a known method (see Patent Documents 1 and 2, for example), followed by decarboxylation. The resulting reaction mixture was subjected to simple distillation to obtain a reaction mixture (1A) (MDJ content: 97.5 mass % (cis isomer content: 10.5 mol %), content of compound (I): 1.0 mass %).

The reaction mixture (1A) was fed to the middle of the purification distillation column 2 illustrated in FIG. 1 (provided with a Sulzer packed column), and subjected to purification distillation (column bottom temperature: 170 to 180° C., pressure: −95.0 to −98.0 kPaG, reflux ratio: 3.5 to 7.0).

The low-boiling fraction (3) (MDJ content: about 93 to 95 mass %, cis isomer content: 2 to 4 mol %, content of compound (I): 0.16 to 0.20 mass %) was continuously extracted from the top of the purification distillation column 2 at a rate of 15 parts by mass per hour. The low-boiling fraction (3) was fed to the isomerization reactor 9.

The high-boiling fraction (5) (MDJ content: 98.8 mass %, cis isomer content: 11.0 mol %, content of compound (I): 1.1 mass %) was continuously extracted from the bottom of the purification distillation column 2 at a rate of 85 parts by mass per hour.

1,000 parts by mass of the fraction (5) was put in the batch-type concentration distillation column 17 (provided with a Sulzer packed column), and subjected to concentration distillation (column bottom temperature: 165 to 175° C., column top temperature: 130 to 140° C., pressure: −95.0 to −98.0 kPaG, reflux ratio: 3.5 to 7.0).

Separately, the fraction (5) was fed to the thin film evaporator 6 at a rate of 85 parts by mass per hour, and subjected to thin film distillation (vapor temperature: 140° C., pressure: −95 to −101.3 kPaG). Product MDJ ("CLAIGEON (registered trademark)" manufactured by Zeon Corporation) (MDJ content: 98.8 mass %, cis isomer content: 11.0 mol %, content of compound (I): 1.1 mass %) was extracted from the top of the thin film evaporator 6 at a rate of 81 parts by mass per hour.

After extracting 60 parts by mass of a low-boiling fraction from the top of the batch-type concentration distillation column 17, 699 parts by mass of an MDJ fraction (18a) having a low cis isomer content (MDJ content: 99.9 mass %, cis isomer content: 2.5 mol %, content of compound (I): 0 mass %) was extracted from the top of the batch-type concentration distillation column 17.

237 parts by mass of a fraction (19a) having a high cis isomer content (MDJ content: 93.5 mass %, cis isomer content: 32.3 mol %, content of compound (I): 4.9 mass %) was extracted from the bottom of the batch-type concentration distillation column 17. 137 parts by mass of the fraction (19a) was fed to the thin film evaporator 14 at a rate of 6 parts by mass per hour, and subjected to thin film distillation (vapor temperature: 140° C., pressure: −95 to −101.3 kPaG). The high-boiling fraction (15) was continuously extracted from the bottom of the thin film evaporator 14 at a rate of 0.3 parts by mass per hour, and recycled to the raw material system 4 that was fed to the purification distillation column 2.

A fraction having a high cis isomer content (MDJ content: 94.9 mass %, cis isomer content: 32.4 mol %, content of compound (I): 4.9 mass %) was extracted from the top of the thin film evaporator 14 at a rate of 5.7 parts by mass per hour. 123 parts by mass of a fraction (16a) was obtained in total. This fraction is referred to as "MDJ composition A".

Example 2

77 parts by mass of the fraction (18a) extracted from the top of the batch-type concentration distillation column 17 in Example 1, and 23 parts by mass of the product MDJ ("CLAIGEON (registered trademark)" manufactured by Zeon Corporation) (MDJ content: 98.8 mass %, cis isomer content: 11.0 mol %, content of compound (I): 1.1 mass %) obtained in Example 1 were mixed using the batch-type isomerization reactor-purification distillation column 20. After the addition of 0.01 parts by mass of sodium carbonate, the mixture was heated at a temperature of 175 to 177° C. for 3 hours under a pressure of 0 to 30 kPaG to effect isomerization. The resulting reaction mixture was subjected to purification distillation (reactor temperature: 160 to 180° C., pressure: −95.0 to −98.0 kPaG), and 90 parts by mass of a fraction (21a) (MDJ content: 99.6 mass %, cis isomer content: 10.9 mol %, content of compound (I): 0.3 mass %) was extracted from the top of the batch-type isomerization reactor-purification distillation column 20.

The fraction (21a) was fed to the batch-type concentration distillation column 17, and subjected to concentration distillation in the same manner as in Example 1. 63 parts by mass of a fraction (18b) (MDJ content: 99.9 mass %, cis isomer content: 2.4 mol %, content of compound (I): 0 mass %) was extracted from the top of the batch-type concentration distillation column 17, and 21 parts by mass of a fraction (19b) (MDJ content: 97.5 mass %, cis isomer content: 32.3 mol %, content of compound (I): 1.1 mass %) was extracted from the bottom of the batch-type concentration distillation column 17. The fraction (19b) was fed to the thin film evaporator 14, and subjected to thin film distillation in the same manner as in Example 1. 19 parts by mass of a fraction (16b) (MDJ content: 98.6 mass %, cis isomer content: 32.3 mol %, content of compound (I): 1.1 mass %) was extracted from the top of the thin film evaporator 14. This fraction is referred to as "MDJ composition B".

Example 3

Isomerization and purification distillation were effected in the same manner as in Example 2, except that 36 parts by mass of the fraction (18a) and 64 parts by mass of the product MDJ were used instead of 77 parts by mass of the fraction (18a) and 23 parts by mass of the product MDJ. A fraction (21b) (MDJ content: 99.1 mass %, cis isomer content: 11.1 mol %, content of compound (I): 0.73 mass %) was extracted from the top of the batch-type isomerization reactor-purification distillation column 20.

The fraction (21b) was subjected to concentration distillation in the same manner as in Example 1. 62 parts by mass of a fraction (18c) (MDJ content: 99.9 mass %, cis isomer content: 2.5 mol %, content of compound (I): 0 mass %) was extracted from the top of the batch-type concentration distillation column 17, and 22 parts by mass of a fraction (19c) (MDJ content: 95.5 mass %, cis isomer content: 32.3 mol %, content of compound (I): 3.1 mass %) was extracted from the bottom of the batch-type concentration distillation column 17.

The fraction (19c) was fed to the thin film evaporator 14, and subjected to thin film distillation in the same manner as in Example 1. 20 parts by mass of a fraction (16c) (MDJ content: 96.6 mass %, cis isomer content: 32.3 mol %, content of compound (I): 3.1 mass %) was extracted from the top of the thin film evaporator 14. This fraction is referred to as "MDJ composition C".

Comparative Example 1

100 parts by mass of the fraction (19a) (MDJ content: 93.5 mass %, cis isomer content: 32.3 mol %, content of compound (I): 4.9 mass %) obtained in Example 1 was subjected to isomerization and purification distillation in the same manner as in Example 2. 90 parts by mass of a fraction (23c) (MDJ content: 94.0 mass %, cis isomer content: 10.9 mol %, content of compound (I): 4.8 mass %) was extracted from the top of the batch-type isomerization reactor-purification distillation column 20.

The fraction (21c) was subjected to concentration distillation in the same manner as in Example 1. 63 parts by mass of a fraction (18d) (MDJ content: 99.8 mass %, cis isomer content: 2.3 mol %, content of compound (I): 0.1 mass %) was extracted from the top of the batch-type concentration distillation column 17, and 21 parts by mass of a fraction (19d) (MDJ content: 78.5 mass %, cis isomer content: 32.1 mol %, content of compound (I): 20.8 mass %) was extracted from the bottom of the batch-type concentration distillation column 17.

The fraction (19d) was fed to the thin film evaporator 14, and subjected to thin film distillation in the same manner as in Example 1. 19 parts by mass of a fraction (16d) (MDJ content: 79.0 mass %, cis isomer content: 32.1 mol %, content of compound (I): 20.7 mass %) was extracted from the top of the thin film evaporator 14. This fraction (16d) is referred to as "MDJ composition D".

Example 4

Isomerization and purification distillation were effected in the same manner as in Example 2, except that 100 parts by mass of the fraction (18a) was used instead of 77 parts by mass of the fraction (18a) and 23 parts by mass of the product MDJ. 90 parts by mass of a fraction (21d) (MDJ content: 99.9 mass %, cis isomer content: 11.0 mol %, content of compound (I): 0 mass %) was extracted from the top of the batch-type isomerization reactor-purification distillation column 20.

The fraction (21d) was subjected to concentration distillation in the same manner as in Example 1. 63 parts by mass of a fraction (20e) (MDJ content: 99.9 mass %, cis isomer content: 2.4 mol %, content of compound (I): 0 mass %) was extracted from the top of the batch-type concentration distillation column 17, and 21 parts by mass of a fraction (19e) (MDJ content: 99.9 mass %, cis isomer content: 32.3 mol %, content of compound (I): 0 mass %) was extracted from the bottom of the batch-type concentration distillation column 17. The fraction (19e) was fed to the thin film evaporator 14, and subjected to thin film distillation in the same manner as in Example 1. 19 parts by mass of a fraction (16e) (MDJ content: 99.9 mass %, cis isomer content: 32.3 mol %, content of compound (I): 0 mass %) was extracted from the top of the thin film evaporator 14. This fraction is referred to as "MDJ reference product 1".

The fraction (16d) obtained in Comparative Example 1 and the fraction (16e) were mixed in a ratio of 5:95 (mass %) to obtain an MDJ composition E (MDJ content: 98.6 mass %, cis isomer content: 32.3 mol %, content of compound (I): 1.2 mass %).

Example 5

The fraction (16d) obtained in Comparative Example 1 and the fraction (16e) obtained in Example 4 were mixed in a ratio of 15:85 (mass %) to obtain an MDJ composition F (MDJ content: 96.8 mass %, cis isomer content: 32.3 mol %, content of compound (I): 3.1 mass %).

Example 6

The fraction (16d) obtained in Comparative Example 1 and the fraction (16e) obtained in Example 4 were mixed in a ratio of 22:78 (mass %) to obtain an MDJ composition G (MDJ content: 95.3 mass %, cis isomer content: 32.3 mol %, content of compound (I): 4.6 mass %).

Comparative Example 2

90 parts by mass of the fraction (18a) extracted from the top of the batch-type concentration distillation column 17 in Example 1 and 10 parts by mass of the fraction (5) extracted from the bottom of the purification distillation column 2 were mixed, and isomerization and purification distillation were effected in the same manner as in Example 2. 90 parts by mass of a fraction (21E) (MDJ content: 99.8 mass %, cis isomer content: 11.2 mol %, content of compound (I): 0.1 mass %) was extracted from the top of the batch-type isomerization reactor-purification distillation column 20.

The fraction (21E) was subjected to concentration distillation in the same manner as in Example 1. 63 parts by mass of a fraction (20f) (MDJ content: 99.9 mass %, cis isomer content: 2.4 mol %, content of compound (I): 0 mass %) was extracted from the top of the batch-type concentration distillation column 17, and 21 parts by mass of a fraction (19f) (MDJ content: 99.2 mass %, cis isomer content: 32.3 mol %, content of compound (I): 0.5 mass %) was extracted from the bottom of the batch-type concentration distillation column 17.

The fraction (19f) was fed to the thin film evaporator 14, and subjected to thin film distillation in the same manner as in Example 1. 19 parts by mass of a fraction (16f) (MDJ content: 99.4 mass %, cis isomer content: 32.3 mol %, content of compound (I): 0.5 mass %) was extracted from the top of the thin film evaporator 14. This fraction (16f) is referred to as "MDJ composition H".

Comparative Example 3

The fraction (16e) obtained in Example 4 and the fraction (16d) obtained in Comparative Example 1 were mixed in a ratio of 98:2 (mass %) to obtain an MDJ composition I (MDJ content: 99.5 mass %, cis isomer content: 32.3 mol %, content of compound (I): 0.4 mass %).

Comparative Example 4

The fraction (16e) obtained in Example 4 and the fraction (16d) obtained in Comparative Example 1 were mixed in a ratio of 66:34 (mass %) to obtain an MDJ composition J (MDJ content: 92.8 mass %, cis isomer content: 32.2 mol %, content of compound (I): 7.04 mass %).

Comparative Example 5

The fraction (16e) obtained in Example 4 and the fraction (16d) obtained in Comparative Example 1 were mixed in a ratio of 50:50 (mass %) to obtain an MDJ composition K (MDJ content: 89.5 mass %, cis isomer content: 32.2 mol %, content of compound (I): 10.4 mass %).

Table 1 shows the MDJ content (mass %), the cis isomer content (mol %) in the MDJ, and the content (mass %) of the compound (I) in the MDJ compositions A to K obtained in Examples 1 to 6 and Comparative Examples 1 to 5 together with the composition of the reference product.

TABLE 1

|  | MDJ composition | MDJ content (mass %) | Cis isomer content (mol %) | Content (%) of compound (I) |
|---|---|---|---|---|
| Reference product |  | 99.9 | 32.3 | 0 |
| Example 1 | Composition A | 94.9 | 32.4 | 4.9 |
| Example 2 | Composition B | 98.6 | 32.3 | 1.1 |
| Example 3 | Composition C | 96.6 | 32.3 | 3.1 |
| Comparative Example 1 | Composition D | 79.0 | 32.1 | 20.7 |
| Example 4 | Composition E | 98.6 | 32.3 | 1.2 |
| Example 5 | Composition F | 96.8 | 32.3 | 3.1 |
| Example 6 | Composition G | 95.3 | 32.3 | 4.6 |
| Comparative Example 2 | Composition H | 99.4 | 32.3 | 0.5 |
| Comparative Example 3 | Composition I | 99.5 | 32.3 | 0.4 |
| Comparative Example 4 | Composition J | 92.8 | 32.2 | 7.04 |
| Comparative Example 5 | Composition K | 89.5 | 32.2 | 10.4 |

Evaluation of MDJ Composition

The smell of the MDJ compositions A to K obtained in Examples 1 to 6 and Comparative Examples 1 to 5 was evaluated as described below.

Smell Evaluation Method

A comparative sensory test (number of panelists: 5) was conducted using the MDJ reference product (content of compound (I): 0 mass %), and the smell of each MDJ composition was evaluated on a 5-point scale (see below). The smell of each MDJ composition was evaluated based on the average points, and an MDJ composition for which the average points were 4 or more was determined to be effective. The panelists also provided their comments on the smell of each MDJ composition.

The evaluation results are shown in Table 2.

Smell Evaluation Criteria and Points 1 point: The smell of the MDJ composition is inferior to that of the MDJ reference product.
2 points: The smell of the MDJ composition is slightly inferior to that of the MDJ reference product.
3 points: The smell of the MDJ composition is equal to that of the MDJ reference product.
4 points: The smell of the MDJ composition is slightly superior to that of the MDJ reference product.
5 points: The smell of the MDJ composition is superior to that of the MDJ reference product.

Table 2 shows the evaluation results (points (upper part) and comments (lower part)) of each panelist.

TABLE 2

|  | Panelist A | Panelist B | Panelist C | Panelist D | Panelist E | Overall evaluation |
|---|---|---|---|---|---|---|
| Reference product 1 | — | — | — | — | — | — |
| Example 1 | 5 | 4 | 5 | 5 | 4 | 4.6 |
|  | Very rich in sweetness | Very rich, but slightly heavy | Very lingering | Deep smell | Very lingering, but slightly heavy |  |
| Example 2 | 4 | 4 | 4 | 5 | 5 | 4.4 |
|  | Rich in sweetness | Rich | Lingering | Deep smell | Very lingering |  |
| Example 3 | 5 | 5 | 5 | 5 | 5 | 5 |
|  | Very rich in sweetness | Very rich | Very lingering | Deep smell | Very lingering |  |
| Comparative Example 1 | 4 | 3 | 4 | 3 | 3 | 3.4 |
|  | Rich | Same | Lingering | Same | Same |  |
| Example 4 | 4 | 5 | 4 | 5 | 5 | 4.6 |
|  | Rich in sweetness | Very rich | Lingering | Deep smell | Very lingering |  |
| Example 5 | 5 | 5 | 5 | 5 | 5 | 5 |
|  | Very rich in sweetness | Very rich | Very lingering | Deep smell | Very lingering |  |
| Example 6 | 5 | 4 | 5 | 4 | 5 | 4.6 |
|  | Very rich in sweetness | Very rich, but slightly heavy | Very lingering | Deep smell, but slightly oily | Very lingering |  |
| Comparative Example 2 | 1 | 1 | 1 | 1 | 1 | 1 |
|  | Heavy | Heavy | Heavy and oily | Oily | Heavy |  |
| Comparative Example 3 | 4 | 3 | 4 | 3 | 3 | 3.4 |
|  | Rich | Same | Lingering | Same | Same |  |
| Comparative Example 4 | 2 | 1 | 2 | 1 | 2 | 1.6 |
|  | Slightly heavy | Heavy | Slightly heavy | Oily | Slightly heavy |  |
| Comparative Example 5 | 2 | 1 | 2 | 1 | 1 | 1.4 |
|  | Slightly heavy | Heavy | Slightly heavy and oily | Oily | Heavy |  |

It was confirmed from the above smell evaluation results that the compound (I) causes methyl dihydrojasmonate to produce a lingering jasmine-like smell with improved richness and depth.

When the content of the compound (I) was too high, methyl dihydrojasmonate produced a heavy and oily smell (Comparative Examples 4 and 5). Therefore, it is considered that the content of the compound (I) is preferably 1 to 5 mass %.

REFERENCE SIGNS LIST

1: Reaction mixture
2: Purification distillation column
3: Low-boiling fraction from top
4: Recycled fraction
5: High-boiling fraction from bottom
6: Thin film evaporator
7: High-boiling fraction (high MDJ content, low cis isomer content) extracted from bottom
8: Fraction (product MDJ) from top
9: Isomerization reactor
10: Gaseous isomerization product
11: Concentration distillation column
12: High-boiling fraction from bottom
13: Low-boiling fraction from top
14: Thin film evaporator
15: High-boiling fraction that is returned to purification distillation column 2
16: MDJ composition (fragrance composition)
17: Batch-type concentration distillation column
18: Low-boiling fraction from top
19: High-boiling fraction from bottom
20: Batch-type isomerization reactor-purification distillation column
21: High-boiling fraction from top

The invention claimed is:

1. A fragrance composition comprising methyl dihydrojasmonate and a compound (I), the fragrance composition containing 94.5 to 99% by mass of the methyl dihydrojasmonate and 1 to 5% by mass of the compound (I), the methyl dihydrojasmonate having a cis isomer content of 20 mol % or more, Compound (I)

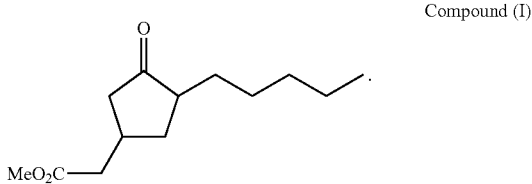 [SMILES: CCCCCC1CC(CC(=O)OC)CC1=O]

2. The fragrance composition according to claim 1, the fragrance composition being obtained by mixing
   a fragrance composition that contains 99% or more by mass of methyl dihydrojasmonate having a cis isomer content of 20 mol % or more and less than 1% by mass of the compound (I) with a fragrance composition that contains 70 to 94.5% by mass of methyl dihydrojasmonate having a cis isomer content of 20 mol % or more and 5 to 30% by mass of the compound (I).

3. A method for producing the fragrance composition according to claim 1, the method comprising subjecting a composition (A) that comprises methyl dihydrojasmonate having a cis isomer content of 20 mol % or more and the compound (I) sequentially to a concentration distillation step and a thin film distillation step,
   the composition (A) containing 90 to 99.5% by mass of the methyl dihydrojasmonate and 0.1 to 1.5% by mass of the compound (I).

4. The method according to claim 3,
   wherein the composition (A) is a high-boiling fraction (5) that is obtained from a bottom of a purification distillation column when a reaction mixture (1) is fed to the purification distillation column to effect purification distillation, the reaction mixture (1) containing methyl dihydrojasmonate having a cis isomer content of less than 20 mol % as a main component, the methyl dihydrojasmonate being obtained by reacting dimethyl malonate with a raw material composition that comprises 2-pentyl-2-cyclopentenone and 2-pentyl-4-cyclopentenone in a mass ratio (2-pentyl-2-cyclopentenone:2-pentyl-4-cyclopentenone) of 95.5:4.5 to 99.5:0.5, followed by decarboxylation.

5. The method according to claim 3,
   wherein the composition (A) is a low-boiling fraction (21) that is obtained from a top of a batch isomerization reactor-purification distillation column (20) when a mixture is fed to the batch isomerization reactor-purification distillation column (20) to effect isomerization and purification distillation,
   the mixture comprising a low-boiling fraction (18) and product MDJ (methyldihydrojasmonate) (8),
   the low-boiling fraction (18) being obtained from a top of a concentration distillation column (17) when a high-boiling fraction (5) that is obtained from the bottom of a purification distillation column (2) when a reaction mixture (1) is fed to the purification distillation column (2) to effect purification distillation,
   the reaction mixture (1) comprising methyl dihydrojasmonate having a cis isomer content of less than 20 mol % as a main component, and
   obtained by reacting dimethyl malonate with the raw material composition that comprises 2-pentyl-2-cyclopentenone and 2-pentyl-4-cyclopentenone in the mass ratio (2-pentyl-2-cyclopentenone:2-pentyl-4-cyclopentenone) of 95.5:4.5 to 99.5:0.5, followed by the decarboxylation,
   the product MDJ (8) being obtained from a top of a thin film evaporator (6) when the high-boiling fraction (5) obtained from the bottom of the purification distillation column (2) is fed to the thin film evaporator (6).

* * * * *